United States Patent [19]

Tanaka et al.

[11] 4,108,663
[45] Aug. 22, 1978

[54] PHOTOGRAPHIC DEVELOPING AGENTS, PROCESS FOR DEVELOPING USING SAME, AND LIGHT-SENSITIVE MATERIALS CONTAINING SAME

[75] Inventors: Mitsugu Tanaka; Masaki Okazaki; Toshiaki Aono; Takeshi Hirose, all of Minami Ashigara, Japan

[73] Assignee: Fuji Photo Film Co., Ltd., Minami Ashigara, Japan

[21] Appl. No.: 738,420

[22] Filed: Nov. 3, 1976

[30] Foreign Application Priority Data

Nov. 7, 1975 [JP] Japan .............................. 50-133693

[51] Int. Cl.² .......................... G03C 3/00; G03C 1/48; G03C/5/30; G03C 1/06
[52] U.S. Cl. ...................................... 96/74; 96/76 R; 96/66.3; 96/95
[58] Field of Search ...................... 96/74, 76, 66.3, 95, 96/3

[56] References Cited

U.S. PATENT DOCUMENTS

| B 351,673 | 1/1975 | Fleckenstein et al. | 96/3 |
|---|---|---|---|
| 3,295,976 | 1/1967 | Abbott et al. | 96/66.3 |
| 3,928,041 | 12/1975 | Fujiwhara et al. | 96/66.3 |
| 3,928,312 | 12/1975 | Fleckenstein | 96/3 |
| 3,931,144 | 1/1976 | Eldredge et al. | 96/3 |
| 3,980,479 | 9/1976 | Fields et al. | 96/3 |

OTHER PUBLICATIONS

Birr–Stabilization of Photographic Silver Halide Emulsions, Focal Press ©1974, N.Y., pp. 115, 116.
Research Disclosure; Feb., 1975; #13024, L. J. Fleckenstein, pp. 37 to 42.

*Primary Examiner*—Dennis E. Talbert, Jr.
*Assistant Examiner*—L. Falasco

*Attorney, Agent, or Firm*—Sughrue, Rothwell, Mion, Zinn and Macpeak

[57] ABSTRACT

A photographic developing agent represented by the formula (I):

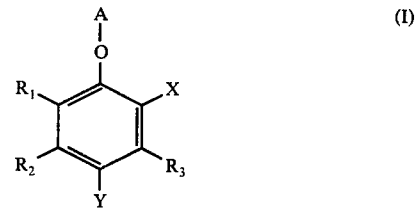

wherein one of X and Y is a group capable of inhibiting development on release immediately after the developing agent is oxidized at the step of development, and the other of X and Y is an $-NH-SO_2-Z$ group (wherein Z is an alkyl group, an aryl group or a heterocyclic group); A is a hydrogen atom or a group hydrolyzable under alkaline conditions; $R_1$, $R_2$, and $R_3$, which may be the same or different, each is a hydrogen atom, an alkyl group, an aryl group, a heterocyclic group, an alkoxy group, an aryloxy group, an $-S-Z'$ group (wherein $Z'$ is an alkyl group, an aryl group or a heterocyclic group), an $-NH-SO_2-Z''$ group (wherein $Z''$ is an alkyl group, an aryl group or a heterocyclic group), an acylamido group, an amino group, a halogen atom, a hydroxy group, or an acyloxy group; and $R_1$ and $R_2$ further may combine to form a ring, a silver halide photographic light-sensitive material having a photographic layer containing at least one compound selected from the compounds represented by the above formula (I), and a process for developing images by treating a photographic light-sensitive material with a developer containing at least one compound selected from the compounds represented by the above formula (I).

12 Claims, No Drawings

PHOTOGRAPHIC DEVELOPING AGENTS, PROCESS FOR DEVELOPING USING SAME, AND LIGHT-SENSITIVE MATERIALS CONTAINING SAME

BACKGROUND OF THE INVENTION

1. Field of the Invention

The present invention relates to a photographic developing agent and more particularly to a photographic developing agent capable of releasing a development inhibitor at the step of development; a silver halide photographic light-sensitive material which has a photographic layer containing the same; and a process for developing images by treating a photographic light-sensitive material with a developer containing the same.

2. Description of the Prior Art

Hitherto, hydroquinone derivatives releasing a development inhibitor depending upon the density of image at the time of development (so-called DIR hydroquinones) are known. Typical examples of known DIR hydroquinones are described in U.S. Pat. Nos. 3,379,529 and 3,620,746, and Japanese Patent Application (OPI) No. 129,536/1974, etc. These DIR hydroquinones are, as described in the above patents, used for the purpose of attaining the so-called DIR effect, e.g., control of image tone, an improvement in graininess, image sharpness and color reproduction, etc.

Although these DIR hydroquinones have desirable properties, they also have various defects. One defect is that a sufficient DIR effect cannot be obtained because of insufficient activity of the compounds. A second defect is that incorporation of the compound into a light-sensitive emulsion layer as a dispersion deteriorates the storage stability of the light-sensitive material. A third defect is that synthesis of the compounds is not easy. A fourth defect is that a reduction in storage stability with time of a coating solution containing the compound deteriorates the photographic properties.

SUMMARY OF THE INVENTION

It has now been found that the photographic developing agents of the present invention are free from the above defects, and have quite excellent properties.

An object of the present invention is to provide an advantageous photographic developing agent.

Another object of the present invention is to provide a photographic developing agent which releases a development inhibitor immediately after being oxidized at the step of development.

A further object of the present invention is to provide a photographic developing agent which does not reduce the storage stability of a light-sensitive material even though it is incorporated into the light-sensitive material.

Further another object of the present invention is to provide a silver halide photographic material contianing the photographic developing agent.

Another object of the present invention is to provide a photographic treating liquid containing the photographic developing agent.

A still further object of the present invention is to provide a process for developing images by effecting development in the presence of the photographic developing agent.

An even further object of the present invention is to provide a photographic developing agent which can be synthesized with ease.

These objects are attained with photographic developing agents which release a development inhibitor after being oxidized and which are represented by the following formula (I)

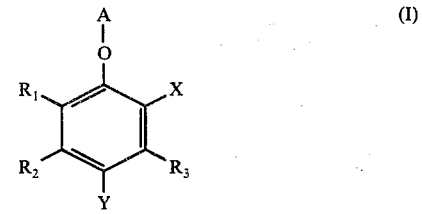

wherein one of X and Y is a group capable of inhibiting development on release immediately after being oxidized at the step of development, and the other of X and Y is an $-NH-SO_2-Z$ group (wherein Z is an alkyl group, an aryl group or a heterocyclic group); A is a hydrogen atom or a group capable of being hydrolyzed under alkaline conditions; $R_1$, $R_2$ and $R_3$, which may be the same or different, each is a hydrogen atom, an alkyl group, an aryl group, a heterocyclic group, an alkoxy group, an aryloxy group, an $-S-Z'$ group (wherein $Z'$ is an alkyl group, an aryl group or a heterocyclic group), an $-NH-SO_2-Z''$ group (wherein $Z''$ is an alkyl group, an aryl group or a heterocyclic group), an acylamino group, an amino group, a halogen atom, a hydroxy group or an acyloxy group; and further $R_1$ and $R_2$ may combine to form a ring.

DETAILED DESCRIPTION OF THE INVENTION

In greater detail, in the formula (I), the group represented by X or Y, which exhibits a development inhibiting action is released immediately after the developing agent is oxidized at the step of development. This development inhibiting group represented by X or Y forms a compound which is strongly adsorbed on the silver halide grains when such is released from the developer nucleus. Such a group is preferably connected through a sulfur atom, a selenium atom or nitrogen atom therein, especially preferably a sulfur atom or a nitrogen atom, to the developing agent mother nucleus (i.e., the phenyl nucleus derived by the removal of X or Y from the formula (I)). Where X or Y is a group which is connected through a sulfur atom therein, an arylthio group, a heterocyclicthio group, a group derived from thioglycolic acid based compounds, and a group derived from cystein or glutathion based compounds are particularly useful and these contain groups, such as $-SCH_2COOH$,

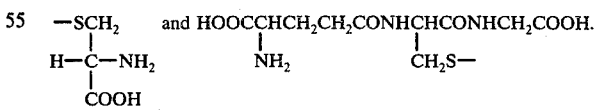

Suitable examples of heterocyclicthio groups include a tetrazolylthio group (e.g., 1-phenyltetrazol-5-ylthio, 1-nitrophenyltetrazol-5-ylthio, 1-naphthyltetrazol-5-ylthio, etc.), a thiazolylthio group (e.g., 2-benzothiazolylthio, 2-naphthothiazolylthio, etc.), an oxadiazolylthio group (e.g., 1,2,4-oxadiazole-5-thio, etc.), a pyrimidinylthio group (e.g., pyrimidinylthio, etc.), a thiazolylthio group (e.g., 1,3,4-thiadiazole-2-thio, etc.), a triazinylthio group (e.g., 1,3,5-triazin-2-ylthio, etc.), triazolylthio group (e.g., 1,2,4-triazolylthio, etc.), and the like.

Suitable examples of the arylthio groups include a phenylthio group (e.g., 2-carboxyphenylthio, 2-nitrophenylthio, 3-heptanamidophenylthio, etc.), and the like. Of these groups, 1-phenyltetrazol-5-ylthio, and 1-nitrophenyltetrazole-5-thio are particularly excellent.

Where X or Y is a group which is connected through a nitrogen atom therein, a triazolyl group, especially a benzotriazolyl group which may be substituted, e.g., 5-methylbenzotriazol-1- or -2-yl, 5-bromobenzotriazol-1- or -2-yl, 5-octanamidobenzotriazol-1- or —2-yl, 5-benzyloxybenzotriazol-1-or —2-yl, 5-(3-methylbenzothiazolinilidene)aminobenzotriazol-1-or —2-yl, and the like are particularly useful.

Where X or Y is an —NHSO$_2$Z group, Z is preferably a straight or branched alkyl group containing 1 to 30 carbon atoms, a substituted alkyl group (with substituents including one or more halogen atoms and alkenyl, aryloxy, hydroxy, allyloxy, carboxy, alkoxycarbonyl, aryloxycarbonyl, sulfo, heterocyclic, aryl, and like groups), an aryl group, e.g., phenyl, and substituted phenyl (in which the number of carbon atoms can be 6 to 36) (with substituents including one or more halogen atoms or alkyl, alkoxy, nitro, cyano, acyl, carboxy, alkoxycarbonyl, acylamino, carbamoyl, sulfamoyl, sulfo, and like groups), a 5-or 6-membered heterocyclic group containing one or more hetero atoms, such as N, O, S, etc., (which group may be condensed with a benzene or naphthalene nucleus), or the like.

Suitable specific examples of Z include methyl, isopropyl, 2-methoxyethyl, octadecyl, benzyl, 3-(4-nitrophenoxy)propyl, 4-(2,4-di-t-pentylphenoxy)butyl, phenyl, 4-tolyl, 4-nonylphenyl, 3-nitrophenyl, 3-(2,4-di-t-pentylphenoxyacetamido)phenyl, 3-[3-(2,4-di-t-pentylphenoxy)propylsulfamoyl]phenyl, pyridyl, imidazolyl, and the like.

Preferred specific examples of groups represented by A, in addition to a hydrogen atom, which are hydrolyzable under alkaline conditions, e.g., at a pH of about 9 to 14, include chloroacetyl, dichloroacetyl, 4-nitrobenzoyl, phenoxycarbonyl, alkoxycarbonyl, alkoxyoxalyl, and the like.

$R_1$, $R_2$ and $R_3$, which can be the same or different, each preferably is a hydrogen atom, a halogen atom, straight or branched substituted or unsubstituted alkyl or alkoxy group (with substituents including one or more halogen atoms and alkoxy, hydroxy, carboxy, sulfo, heterocyclic, aryl, and like groups) containing 1 to 30 carbon atoms, an acylamino group, a substituted or unsubstituted aryl or aryloxy group containing 6 to 36 carbon atoms (with substituents including one or more halogen atoms and alkyl, alkoxy, and like groups), a 5- or 6-membered heterocyclic group containing one or more hetero atoms such as N, O, S, etc., (which group may be condensed with a benzene or naphthalene nucleus), a substituted or unsubstituted amino group (with substituents including one or more alkyl, aryl, heterocyclic, and like groups containing 1 to 30 carbon atoms), an —SZ′ group, and an —NHSO$_2$Z″ group (where Z′ and Z″ are the same as Z defined for X or Y, and Z, Z′ and Z″ may be the same or different), and the like.

$R_1$ and $R_2$ may combine with each other to form a substituted or unsubstituted saturated or unsaturated ring (with substituents including those as described by $R_1$, $R_2$ and $R_3$, and with typical developing agent mother nuclei being formed by the combination of $R_1$ and $R_2$ with each other, are saturated carbon rings and unsaturated carbon rings, such as a naphthalene nucleus, a tetralin nucleus, which are preferably used in the present invention). $R_1$, $R_2$ and $R_3$ may be the same or different.

Preferred specific examples of $R_1$, $R_2$ and $R_3$ are hydrogen, halogen, methyl, ethyl, isopropyl, 2-chloroethyl, t-octyl, dodecyl, octadecyl, methoxy, octoxy, benzyloxy, acetamido, trifluoroacetamido, tetradecanamido, benzamido, phenyl, 4-methylphenoxy, pyridyl, imidazolyl, and the like.

Further, with respect to the above described groups for X, Y and $R_1$–$R_3$, the number of carbon atoms for the alkyl groups, the alkyl moieties present in the above described groups or the alkenyl groups can range from 1 to 30, preferably from 1 to 25. Further, the aryl groups or aryl moieties can be either monocyclic groups or moieties (e.g., phenyl) or polycyclic groups or moieties (e.g., naphthyl). Additionally, suitable heterocyclic groups include 5- or 6-membered rings containing at least one of a nitrogen atom, a sulfur atom or an oxygen atom as a hetero atom, which heterocyclic ring may be condensed with an aromatic ring (e.g., a benzene ring) and examples of halogen atoms or halogen substituents include a fluorine atom, a bromine atom and a chlorine atom.

Particularly useful photographic developing agents of the present invention are represented by the following formula (II):

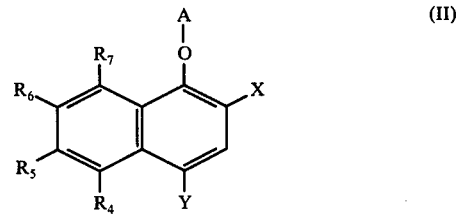

wherein $R_4$ through $R_7$ each represents a hydrogen atom, a halogen atom, an unsubstituted or substituted alkyl (straight or branched) group containing 1 to 30 carbon atoms (with substituents including one or more halogen atoms and alkoxy, hydroxy, carboxy, sulfo, heterocyclic, aryl and like groups), a straight or branched unsubstituted or substituted alkoxy group containing 1 to 30 carbon atoms (with substituents including the same as described for the above substituted alkyl group), an unsubstituted or substituted phenyl group whose total number of carbon atoms is 6 to 36 (with substituents including one or more halogen atoms and alkyl, alkoxy and like groups), an unsubstituted or substituted phenyloxy group (with substituents including the same as described for the substituted phenyl group), a 5- or 6-membered heterocyclic group containing one or more hetero atoms such as N, O, S, etc. (which may be condensed with a benzene or naphthalene nucleus), an acylamino group, a sulfonamido group, a carbamoyl group, a sulfamoyl group, an acyl group, an alkoxycarbonyl group, an alkylthio group, and the like. $R_4$, $R_5$, $R_6$ and $R_7$ may be the same or different. X, Y and A are the same as defined in the formula (I).

It is further particularly preferred for the developing agent of this invention to have the general formula (III):

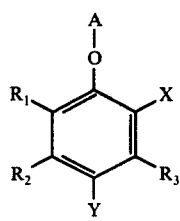
(III)

wherein one of X and Y is a group capable of inhibiting development on release immediately after the developing agent is oxidized at development, and the other of X and Y is an —NHSO$_2$—Z group, wherein Z contains 1 to 30 carbon atoms and is an alkyl group, an aryl group, or a 5- or 6-membered heterocyclic group; A is a hydrogen atom or a group hydrolyzable under alkaline conditions; $R_1$, $R_2$ and $R_3$, which may be the same or different, is a hydrogen atom, a halogen atom, an alkyl group containing 1 to 30 carbon atoms, an alkoxy group containing 1 to 30 carbon atoms, an aryl group, an aryloxy group, an amino group, an —SZ′ group, or an —NHSO$_2$Z″ group, wherein Z′ and Z″, which may be the same or different, each is as described above for Z, and $R_1$ and $R_2$ further may combine together to form a saturated or unsaturated ring.

Typical examples of the photographic developing agents represented by the formula (I) are as follows:

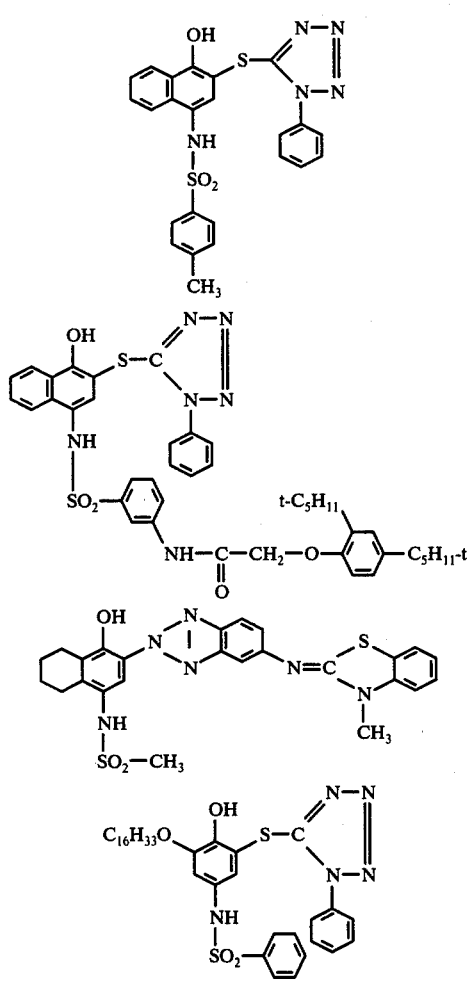

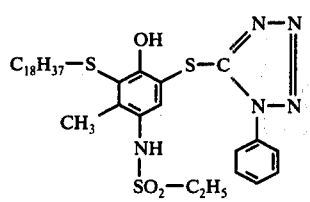

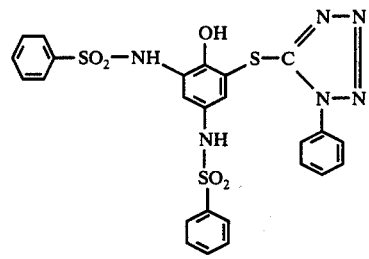

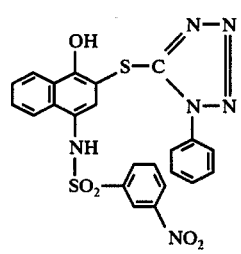

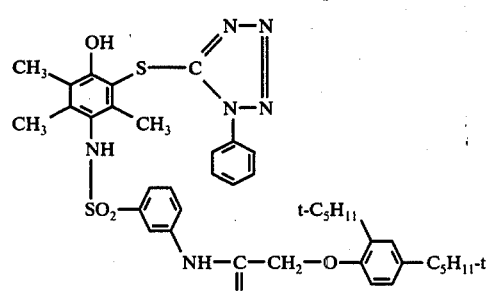

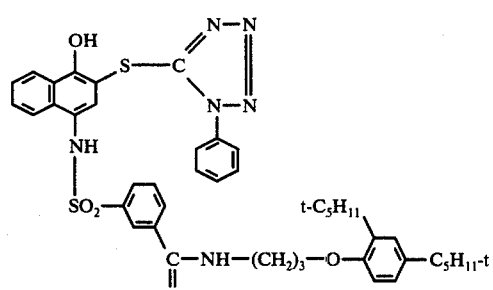

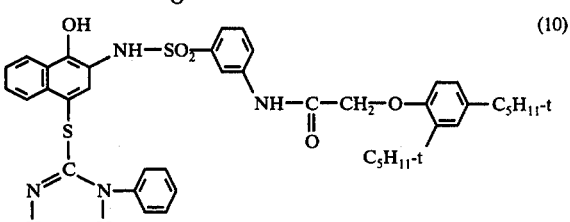

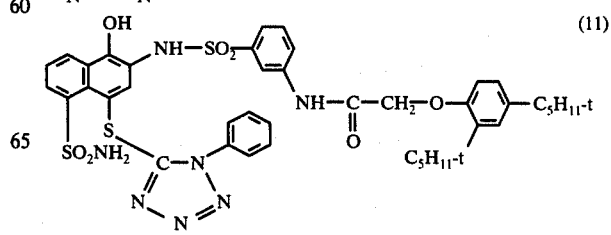

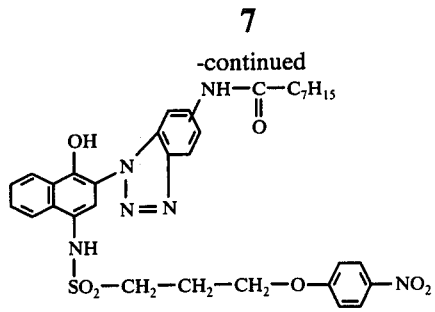

Of the above compounds, those compounds in which the developing agent mother nucleus and the group exhibiting a development inhibiting action are bonded together through a sulfur atom in the development-inhibiting group can be easily prepared, for example, by reacting sulfenyl chloride, XCl or YCl, which have been prepared by reacting XH or YH (where X and Y are the same as defined in the formula (I)) with chlorine gas or sulfuryl chloride, with the developing agent mother nucleus at the active position thereof.

On the other hand, those compounds in which the developing agent mother nucleus and the group exhibiting a development inhibiting action are bonded together through a nitrogen atom in the development-inhibiting group can be easily prepared, for example, by a method which comprises coupling a substituted or unsubstituted o-nitrophenyl diazonium salt to the active position of the developing agent mother nucleus, and then reducing and closing the ring to thereby produce a triazole ring, as in the method described in U.S. Pat. No. 3,617,291.

A suitable temperature which can be used for the reactions described above ranges from about 0° to 50° C with a suitable molar ratio of reactants being about 1:1. In general, the reaction takes about 2 to 3 hours and is generally conducted in a solvent such as chloroform, carbon tetrachloride, dimethylformamide, or the like.

Typical methods of synthesizing the compounds of the present invention are shown below. Other compounds can be produced in an analogous way to the following examples.

PREPARATION EXAMPLE 1

Compound (7)

In 100 ml of carbon tetrachloride was dispersed 68 g (0.038 mol) of 1-phenyl-5-mercaptotetrazole. A sulfenyl chloride compound was produced by feeding chlorine gas until the contents became uniform. This compound was added to 13.4 g (0.038 mol) of 4-(3-nitrobenzenesulfonamido)-1-naphthol dissolved in 70 ml of dimethylformamide, which was then stirred at room temperature (about 25° C) for 2 hours. The reaction mixture was poured onto ice water and extracted with ethyl acetate. The solvent was distilled away from the extract and the residue so obtained was recrystallized from a mixed solvent of methanol and ethanol (2:1 by volume). Thus, 16.5 g of Compound (7) having a melting point of 170° C was obtained. Yield 89%.

PREPARATION EXAMPLE 2

Compound (1)

Compound (1) having a melting point of 206° to 207° C was produced in the same manner as used in Preparation Example 1 except that 4-(p-toluenesulfonamido)-1-naphthol was used in place of 4-(3-nitrobenzenesulfonamido)-1-naphthol. Acetonitrile was used as the recrystallization solvent. Yield 94%.

PREPARATION EXAMPLE 3

Compound (2)

Compound (2) having a melting point of 130° to 132° C was produced in the same manner as used in Preparation Example 1 except that 4-[3-(2,4-di-tert-pentylphenoxyacetamido)benzenesulfonamido]-1-naphthol was used in place of 4-(3-nitrobenzenesulfonamido)-1-naphthol. Benzene was used as the recrystallization solvent. Yield 87%.

PREPARATION EXAMPLE 4

Compound (9)

Compound (9) having a melting point of 108° to 111° C was produced in the same manner as used in Preparation Example 1 except that 4-{3-[γ-(2,4-di-tert-pentylphenoxy)propylcarbamoyl]benzenesulfonamido}-1-naphthol was used in place of 4-(3-nitrobenzenesulfonamido)-1-naphthol. Chloroform was used as the recrystallization solvent. Yield 91%.

The photographic developing agents of the present invention can be incorporated into either a photographic emulsion layer or a developer. Where the photographic developing agents of the present invention are incorporated into the photographic emulsion layer to provide anti-diffusion properties thereto, all of the known ballast groups can be used. These ballast groups are described in many patents, e.g., U.S. Pat. Nos. 2,920,961, 3,926,634 and 3,891,445.

Examples of suitable ballast groups which can be used include substituted or unsubstituted alkyl groups having at least 5 carbon atoms, substituted or unsubstituted alkoxy groups having at least 5 carbon atoms, sulfonamido groups having at least 5 carbon atoms, aryl or aryloxy groups having at least 6 carbon atoms, alkyl- or heterocyclic-thio groups having at least 5 carbon atoms, arylthio groups having at least 6 carbon atoms, acylamino or acyloxy groups having at least 5 carbon atoms, and heterocyclic groups having at least 4 carbon atoms. The number of carbon atoms in the ballast group can range from about 6 to 30 and the alkyl group or moiety of the ballast group can either be straight or branched chain.

It is anticipated that the developing agents of the present invention are, as are the DIR hydroquinones described in U.S. Pat. No. 3,379,529, etc., subjected to cross-oxidation through a redox reaction thereof and the developing agent oxidants are imagewise produced at the time of color development, thereby imagewise releasing development inhibiting materials and being converted into colorless oxidants. Herein, the development inhibiting materials imagewise released cause intra-image effect and inter-image effect in the light-sensitive material, and exhibit DIR effects, e.g., an improvement in graininess, a softening of image tone, an improvement in image sharpness and an improvement in color reproduction, etc. It is quite surprising that the developing agents of the present invention are highly active and that almost no reduction in sensitivity with time occurs, as compared with the conventional DIR hydroquinones. Since the developing agents of the present invention are substantially colorless or are only very slightly pale blue, from a practical standpoint they have substantially no influence.

The photographic developing agents of the present invention can be dispersed and incorporated into a photographic layer using known methods. In this case, they can be used individually or in admixture with each other. The photographic developing agents of the present invention can be used in combination with couplers and added to the same emulsion layer as the coupler, or added to auxiliary photographic layers such as an intermediate layer and the like as independent emulsions.

The photographic developing agent of the present invention when incorporated in the photographic element is used in an amount of 0.1 to 50 mol%, preferably 0.3 to 15 mol%, based upon the coupler(s) contained in each of the light-sensitive layers in which the developing agent is incorporated: yellow coupler in the blue-sensitive layer, magenta coupler in the green-sensitive layer, or cyan coupler in the red-sensitive layer.

Color-forming couplers which can be used in the present invention include those compounds listed below. These couplers may be either four-equivalent or two-equivalent. Also, they can be either colored couplers for color correction or couplers (DIR couplers) releasing development inhibiting agents.

As yellow image-forming couplers, known open-chain ketomethylene based couplers can be used. Of these couplers, benzoylacetanilide based and pivaloylacetanilide based compounds are particularly useful. Representative examples of the yellow image-forming couplers which can be used in the present invention are described in U.S. Pat. Nos. 2,875,057, 3,265,506, 3,341,331, 3,369,895, 3,408,194, 3,551,155, 3,582,322, 3,725,072, West German Patent Publication No. 1,547,868, West German Patent Application (OLS) Nos. 2,057,941, 2,162,899, 2,213,461, 2,219,917, 2,261,361, 2,263,875, etc.

As the magenta image-forming couplers, pyrazolone based compounds, indazolone based compounds, cyanoacetyl compounds, and the like can be used. Of these compounds, the pyrazolone based compounds are useful. Representative examples of the magenta image-forming couplers which can be used in the present invention are described in U.S. Pat. Nos. 2,439,098, 2,600,788, 2,983,608, 3,311,476, 3,419,391, 3,519,429, 3,558,319, 3,582,322, 3,615,506, British Pat. No. 956,261, West German Patent No. 1,810,464, West German Patent Application (OLS) Nos. 2,408,665, 2,418,959, 2,424,467, Japanese Patent Publication No. 2016/1969, etc.

As the cyan image-forming couplers, phenol derivatives, naphthol derivatives, and the like can be used. Representative examples of these compounds are described in U.S. Pat. Nos. 2,369,924, 2,434,272, 2,474,293, 2,600,788, 2,698,794, 2,706,684, 2,895,826, 3,034,892, 3,214,437, 3,253,924, 3,311,476, 3,386,830, 3,458,315, 3,560,212, 3,582,322, 3,583,971, 3,591,383, West German Patent Application (OLS) Nos. 2,163,811, 2,414,006, Japanese Patent Publication Nos. 6031/1965, 28836/1970, etc.

Those image forming couplers which can be used in the present invention are described in Japanese Patent Publication No. 2016/1969, U.S. Pat. Nos. 2,434,272, 3,476,560, 3,476,564, West German Patent Application (OLS) No. 2,418,959 (magenta image-forming); and Japanese Patent Publication Nos. 22335/1963, 20591/1966, 11304/1967, 32461/1969, U.S. Pat. Nos. 3,034,892, 3,386,830 (cyan image-forming), etc.

As the DIR couplers, those compounds having groups which form development inhibiting agents as coupling releasable groups can be used. These compounds are described in U.S. Pat. Nos. 3,148,062, 3,214,437, 3,227,554, 3,253,924, 3,617,291, 3,622,328, 3,639,417, 3,701,783, 3,705,201, 3,770,436, 3,790,384, Japanese Patent Publication No. 28836/1970, West German Patent Application (OLS) Nos. 2,414,006, 2,417,914, etc.

The above couplers, etc., can be incorporated into a single layer in admixture with each other in order to satisfy the properties required for a light-sensitive material, and alternatively one compound can be incorporated into two or more different layers.

Incorporation of the coupler can be carried out using known methods, for example, the method described in U.S. Pat. No. 2,322,027. That is to say, the coupler is dissolved in an organic solvent having a boiling point of not less than about 180° C, such as phthalic acid alkyl esters (e.g., dibutyl phthalate, dioctyl phthalate, and the like), trimellitic acid esters (e.g., tri-tert-octyl trimellitate), phosphoric acid esters (e.g., diphenyl phosphate, triphenyl phosphate, tricresyl phosphate, dioctyl butyl phosphate, and the like), citric acid esters (e.g., tributyl acetylcitrate), alkylamides (e.g., N,N-diethyllaurylamide, and the like), etc., or in an organic solvent having a boiling point of about 30° to 150° C, such as lower alkyl acetates, e.g., ethyl acetate, butyl acetate, ethyl propionate, sec-butyl alcohol, methyl isobutyl ketone, β-ethoxyethyl acetate, methyl Cellosolve acetate, and the like, and then dispersed in a hydrophilic colloid. The high boiling organic solvents and low boiling organic solvents can be used in admixture with each other.

Where the coupler has an acid group, such as a carboxylic acid group, a sulfonic acid group, or the like, the coupler can be incorporated into a hydrophilic colloid as an alkaline aqueous solution.

The color-image forming coupler is generally employed in an amount of about $2 \times 10^{-3}$ mol to about $5 \times 10^{-1}$ mol, preferably $1 \times 10^{-2}$ mol to $5 \times 10^{-1}$ mol, per mol of silver in the emulsion layer.

The color development processing used in treating a color light-sensitive material in the presence of the developing agent of the present invention comprises fundamentally the steps of color development, bleaching, and fixing. Each step can be carried out independently, or two or more steps can be carried out at the same time by using a treating solution capable of simultaneously achieving each of the steps combined. For example, a one-bath bleaching and fixing solution can be employed. Also, each step can be divided into two or more steps as necessary, and carried out. Alternatively, a combination of color development, first fixing, and bleaching-fixing can be employed. In combination with the step of development, various steps such as pre-hardening, neutralizing, first development (black-and-white development), image stabilizing, washing, etc., can be carried out, if necessary. The preferred processing temperature range will be dependent upon the light-sensitive material and processing involved. Sometimes the temperature employed is below about 18° C, but usually the temperature is above about 18° C. The processing temperature especially often used is about 20° C to about 60° C, and recently it is particularly within the range of about 30° C to about 60° C. It is not always necessary that the series of processing steps be carried out at the same temperature.

A color developer is an alkaline aqueous solution containing a developing agent and having a pH of 8 or more, preferably 9 to 12.

The above developing agent designates a compound having a primary amino group at the aromatic nucleus thereof and capable of developing silver halide, or a precursor of such a compound. Preferred developing agents include 4-amino-N,N-diethylaniline, 3-methyl-4-amino-N,N-diethylaniline, 4-amino-N-ethyl-N-β-hydroxyethyl aniline, 3-methyl-4-amino-N-ethyl-N-β-hydroxyethyl aniline, 4-amino-3-methyl-N-ethyl-N-β-methanesulfonamidoethyl aniline, 4-amino-N,N-dimethyl aniline, 4-amino-3-methoxy-N,N-diethyl aniline, 4-amino-3-methyl-N-ethyl-N-β-methoxyethyl aniline, 4-amino-3-methoxy-N-ethyl-N-β-methoxyethyl aniline, 4-amino-3-β-methanesulfonamidoethyl-N,N-diethyl aniline, and the salts (for example, sulfates, hydrochlorides, sulfites, p-toluenesulfonic acid salts, and the like) thereof. In addition, those compounds described in U.S. Pat. Nos. 2,193,015, 2,592,364, Japanese Patent Application (OPI) No. 64933/1973, and L. F. A. Mason, *Photographic Processing Chemistry*, pp. 226 to 229, Focal Press-London Edition (1966), etc., can be used. Also, the above compounds can be used in combination with 3-pyrazolidones. To the color developer is added various kinds of additives, if necessary.

Typical additives include alkali agents (e.g., the hydroxides, carbonates, and phosphates of alkali metals or ammonia); pH controlling agents or buffers (e.g., weak acids such as acetic acid, boric acid, weak bases, and the salts thereof); development accelerating agents (e.g., those described in U.S. Pat. Nos. 2,648,604, 3,671,247, 2,533,990, 2,577,127, 2,950,970, British Pat. Nos. 1,020,033, 1,020,032, U.S. Pat. No. 3,068,097, etc.); antifogging agents, (e.g., alkali metal bromides, alkali metal iodides, nitrobenzoimidazoles described in U.S. Pat. Nos. 2,496,940, 2,656,271, mercaptobenzoimidazole, 5-methylbenzotriazole, 1-phenyl-5-mercaptotetrazole, and antifogging agents described in U.S. Pat. Nos. 3,113,864, 3,342,596, 3,295,976, 3,615,522, 3,597,199, British Pat. No. 972,211, Japanese Patent Publication No. 41675/1971, *Kagaku Shashin Binran* (*Handbook of Scientific Photography*), 2nd Ed., pp. 29 to 47); and stain or sludge preventing agents and preservatives (e.g., sulfites, bisulfites, hydroxylaminehydrochlorides, formsulfites, alkanolamine sulfite adducts, etc.), as described in U.S. Pat. Nos. 3,161,513, 3,161,514, British Pat. Nos. 1,030,442, 1,144,481, 1,251,558.

During this series of color developing processing steps, intensification processings as described in West German Patent Application (OLS) No. 2,226,770, U.S. Pat. No. 3,826,652, etc., can be employed.

In effecting black-and-white development, well known developing agents and combinations thereof are widely used. With regard to additives which can be incorporated into the processing solution, almost the same additives as in color development processing can be used.

Although the amount of the photographic developing agent of the present invention employed will vary depending upon the light-sensitive material and the type of development, where the developing agent is contained in the light-sensitive material, an especially useful range is about 0.0005 to about 0.5 mol, per mol of silver halide contained in the emulsion. Also, where the photographic developing agent is incorporated into the developer, a range of about $1 \times 10^{-4}$ mol to about $1 \times 10^{-1}$ mol, per 1000 ml of the developer is particularly useful.

The silver halide photographic emulsions as herein used are those prepared by dispersing a light-sensitive silver halide such as silver chloride, silver bromide, silver chlorobromide, silver chloroiodide, silver iodobromide, and silver chloroiodobromide in a hydrophilic polymer material such as gelatin in the form of colloidal particles, and they can be produced by various methods. To the silver halide photographic emulsion can be added various well-known additives such as chemical sensitizers, stabilizers, anti-fogging agents, hardeners, spectral sensitizers, surface active agents, and the like, which are usually added to conventional silver halide photographic emulsions. The photographic emulsion can be coated on a suitable support using well-known methods. A suitable coating amount of silver where the image is to be observed using transmitted light through the photographic element can range from about 0.5 to 3 g/m² when the molar ratio of the silver to the dye image forming coupler is about 10 (in general, the molar ratio of silver to the coupler can range from about 2 to 150). Where the image is to be observed using reflected light from the photographic element, a suitable coating amount of silver per unit area is about half that amount required for a photographic element to be viewed with transmitted light.

The photographic developing agents of the present invention can be used after being emulsified in combination with reducing agents such as hydroquinone and its derivatives, catechol and its derivatives, aminophenol and its derivatives, ascorbic acid and its derivatives, and the like.

Specific examples of benzenes having at least one hydroxy group which can be used are described in British Pat. Nos. 558,258, 557,750, 557,802, 752,146, 1,086,208, U.S. Pat. Nos. 3,700,453, 2,701,197, 2,899,334, 2,728,659, 2,336,327, 2,732,300, 2,403,721, 3,243,294, 3,816,126, 3,582,333, *Chemical Abstracts*, Vol. 58, 6367h, German Patent Application (OLS) Nos. 2,149,789, 2,505,016, Japanese Patent Application (OPI) Nos. 156438/1975, 106329/1974 and Japanese Patent Publication No. 21249/1975. A suitable molar ratio of these reducing agents to the developing agent of the present invention can range from about 1 to 100% by weight.

A light-sensitive material containing the photographic developing agent of the present invention can be subjected to color development using aromatic primary amine compounds such as derivatives of p-phenylenediamine, and also it can be subjected to black-and-white development using a developer containing a well-known black-and-white developing agent.

The photographic developing agents of the present invention can be employed in either a color developer or a black-and-white developer.

Useful photographic supports for use in the light-sensitive material of the present invention are films of semi-synthetic or synthetic polymers, such as cellulose acetate, polystyrene, polyethylene terephthalate, polycarbonate, and the like, a paper coated or laminated with baryta or an α-olefin polymer (e.g., polyethylene, polypropylene, an ethylene-butene copolymer, or the like).

The photographic developing agents of the present invention can be used in various kinds of silver halide photographic light-sensitive materials, and they are useful either for black-and-white light-sensitive materials or for color light-sensitive materials. Also, they can be used in silver halide photographic light-sensitive materials having various applications, for example, black-and-white materials for general use, black-and-white materials for printing, X-ray recording materials, electron ray recording materials, black-and-white materials for high resolution, general color materials, color X-ray recording materials, diffusion transfer type color materials, etc.

In a multi-layer color light-sensitive material, as an embodiment of the present invention, which includes a blue-sensitive emulsion layer unit composed of one or more silver halide emulsion layers containing a yellow image-forming coupler which is sensitive mainly to blue light (wavelength: not more than about 500 nm) and is capable of forming a yellow dye on coupling with an oxidized primary aromatic amino developing agent, a green-sensitive emulsion layer unit composed of one or more silver halide emulsion layers containing a magenta image-forming coupler which is sensitive mainly to green light (wavelength: about 500 to about 600 nm) and is capable of forming a magenta dye on coupling with an oxidized primary aromatic amino developing agent, and a red-sensitive emulsion unit composed of one or more silver halide emulsion layers containing a cyan image-forming coupler which is sensitive mainly to red light (wavelength: not less than about 590 nm) and is capable of forming a cyan dye on coupling with an oxidized primary aromatic amino developing agent; and which can include auxiliary photographic layers such as an intermediate layer and the like, the compounds of the present invention can be incorporated into the above described emulsion layers or intermediate layers.

In the above embodiment, the emulsion layers forming the blue-sensitive emulsion layer unit, the green-sensitive emulsion layer unit, and the red-sensitive emulsion layer unit can be arranged in various orders depending upon the end-use application of the light-sensitive material. For instance, where each emulsion layer unit is composed of one emulsion layer, the red-sensitive emulsion layer, the green-sensitive emulsion layer, and the blue-sensitive emulsion layer can be present on the support in this order, or this order can be changed. Where any one of the emulsion layer units is composed of two or more emulsion layers, they can be adjacent to each other or they can be interposed between emulsion layers of other emulsion layer units.

A multi-layer color light-sensitive material is also useful which has on the support thereof a red-sensitive silver halide light-sensitive emulsion layer unit containing an uncolored cyan coupler and a non-diffusible colored cyan coupler and capable of providing a cyan image through color development; a green-sensitive silver halide light-sensitive emulsion layer unit containing an uncolored magenta coupler and a non-diffusible colored magenta coupler and capable of providing a magenta image; and a blue-sensitive silver halide light-sensitive emulsion layer unit containing a non-diffusible uncolored yellow coupler and capable of providing a yellow image, in which the developing agents of the present invention are incorporated into the red-sensitive emulsion layer unit, the green-sensitive emulsion layer unit, and the blue-sensitive emulsion layer, or in intermediate layers.

Since the photographic developing agents of the present invention are very active, development inhibiting agents are released immediately after oxidation. Thus the addition of the photographic developing agent of the present invention in a small amount enables achievement of excellent DIR effects, that is to say, control of image tone, improvement in graininess, image sharpness and color reproduction, etc. Furthermore, since the photographic developing agents of the present invention are stable even though they are present in the light-sensitive emulsion and do not degrade the storage stability of the light-sensitive material, they can be used without any concern. Moreover, the photographic developing agents of the present invention can be quite easily synthesized as shown in Preparation Examples above.

The present invention will be described in greater detail by reference to the following Examples although the invention is not intended to be construed to be limited thereto. Unless otherwise indicated, all parts, percents, ratios and the like are by weight.

EXAMPLE 1

Preparation of Sample 101

1 kg of a conventional silver iodobromide emulsion (amount of silver: 0.6 mol; I content: 6 mol%) was subjected to spectral sensitization using $4 \times 10^{-5}$ mol per mol of silver of Sensitizing Dye I (set forth below) and $1 \times 10^{-5}$ mol per mol of silver of Sensitizing Dye II. 100 g of Coupler A was dissolved in 100 ml of tricresyl phosphate and 200 ml of ethyl acetate, and emulsified in 1 kg of a 10% gelatin aqueous solution using 4 g of sodium nonylbenzene sulfonate to produce Emulsion (I). 280 g of Emulsion (I) was added to 1 kg of the above spectrally sensitized silver iodobromide emulsion and stirred, to which 1.4 g of sodium 2,4-dichloro-6-hydroxy triazine as an aqueous solution thereof was added as a hardening agent. The thus-prepared coating solution was coated on a transparent cellulose triacetate film support so as to provide a silver coating amount of 1.5 g/m². Then a solution prepared by adding 2 g of sodium 2,4-dichloro-6-hydroxy triazine to 1 kg of a 10% aqueous gelatin solution was coated thereon to provide a protective layer having a dry film thickness of 1.5 microns.

Preparation of Samples 102 and 103

Samples 102 and 103 were produced in the same manner as Sample 101 except that Compounds (2) and (7) were further added to the tricresyl phosphate/ethyl acetate mixture of Emulsion (I) of Sample 101 in an amount of 3 mol% based upon Coupler A.

Preparation of Sample 111

1 kg of a silver iodobromide emulsion (the same as used in Sample 101) was subjected to spectral sensitization using $3 \times 10^{-5}$ mol per mol of silver of Sensitizing Dye III and $1 \times 10^{-5}$ mol per mol of silver of Sensitizing Dye IV. 400 g of Emulsion (II) prepared in the same manner as in Emulsion (I) of Sample 101, except that 100 g of Coupler B was used in place of Coupler A, was added thereto, and furthermore, 1.4 g of sodium 2,4-dichloro-6-hydroxy triazine as an aqueous solution thereof was added with stirring. The thus-obtained coating solution was coated in the same manner as in Sample 101. Furthermore, a protective layer was coated in the same manner as in Sample 101.

Preparation of Samples 112 and 113

Samples 112 and 113 were produced in the same manner as in Sample 111 except that Compound (2) and Compound (7), respectively, were further added to the tricresyl phosphate/ethyl acetate mixture of the emulsion of Sample 111 in an amount of 3 mol% based upon Coupler B.

Preparation of Sample 121

To 1 kg of a silver iodobromide emulsion (the same as used in Sample 101) was added 420 g of Emulsion (III) which had been prepared in the same manner as in Emulsion (I) of Sample 101, except that 100 g of Coupler C was used in place of Coupler A. Furthermore, 1.4 g of sodium 2,4-dichloro-6-hydroxy triazine as the aqueous solution thereof was added thereto with stirring to thereby produce a coating solution. This coating solution was coated on the same kind of support as used in Sample 101, and then a protective layer was coated as in Sample 101. Thus Sample 121 was obtained.

Preparation of Samples 122 and 123

Samples 122 and 123 were produced in the same manner as in Sample 121, except that Compound (2) and Compound (7), respectively, were further added to the tricresyl phosphate/ethyl acetate mixture of the emulsion of Sample 121 in an amount of 3 mol% based upon Coupler C.

Compounds used in preparing the above samples

Sensitizing Dye I:
Anhydro-5,5'-dichloro-3,3-di-sulfopropyl-9-ethyl-thiacarbocyanine hydroxide pyridinium salt Sensitizing Dye II:
Anhydro-9-ethyl-3,3'-di-(3-sulfopropyl)-4,5,4',5'-dibenzothiacarbocyanine hydroxide triethylamine salt Sensitizing Dye III:
Anhydro-9-ethyl-5,5'-dichloro-3,3'-sulfopropyloxacarbocyanine sodium salt Sensitizing Dye IV:
Anhydro-5,6,5,6-tetrachloro-1,1-diethyl-3,3-sulfopropoxyethoxyethylimidazolonecarbocyanine hydroxide sodium salt Coupler A:
1-Hydroxy-N-[γ-(2,4-di-tert-amylphenoxypropyl]-2-naphthamide Coupler B:
1-(2,4,6-Trichlorophenyl)-3-[3-(2,4-di-tert-amylphenoxyacetamido)benzamido]-5-pyrazolone Coupler C:
α-(2,4-Dioxo-5,5-dimethyloxazolydinyl)-α-pivaloyl-2-chloro-5-[α-(2,4-di-tert-amylphenoxy)-butanamido]acetanilide Samples 101, 102 and 103 were subjected to stepwise red exposure, Samples 111, 112 and 113 were subjected to stepwise green exposure, and Samples 121, 122 and 123 were subjected to stepwise blue exposure. These exposed samples were then developed at 38° C using the following steps.

| 1. | Color Development | 3 min and 15 sec |
|---|---|---|
| 2. | Bleaching | 6 min and 30 sec |
| 3. | Water Washing | 3 min and 15 sec |
| 4. | Fixing | 6 min and 30 sec |
| 5. | Water Washing | 3 min and 15 sec |
| 6. | Stabilizing | 3 min and 15 sec |

The composition of the processing solutions used in each step was as follows:

| Color Developer | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxyamine Sulfate | 2.4 g |
| 4-[N-Ethyl-N-(β-hydroxyethyl)amino]-2-methyl-aniline Sulfate | 4.5 g |
| Water to make | 1 l |

| Bleaching Solution | |
|---|---|
| Ammonium Bromide | 160.0 g |
| Ammonia (28% aq. soln.) | 25.0 ml |
| Sodium Ethylenediaminetetraacetato-ferrate (III) | 130 g |
| Glacial Acetic Acid | 14 ml |
| Water to make | 1 l |

| Fixing Solution | |
|---|---|
| Sodium Tetrapolyphosphate | 2.0 g |
| Sodium Sulfite | 4.0 g |
| Ammonium Thiosulfate (70% aq. soln.) | 175.0 ml |
| Sodium Hydrogensulfite | 4.6 g |
| Water to make | 1 l |

| Stabilizing Solution | |
|---|---|
| Formaldehyde (40% aq. soln.) | 8.0 ml |
| Water to make | 1 l |

The color density of Samples 101 to 103, Samples 111 to 113 and Samples 121 to 123 was measured using red light, green light and blue light. The characteristics obtained (relative inertia sensitivity Si, gradation γ) are shown in Table 1.

TABLE 1

| Sample | Main Coupler | DIR Compound | Si | γ |
|---|---|---|---|---|
| 101 | Cyan Coupler A | — | 100 | 1.70 |
| 102 | " | Compound (2) | 97 | 0.90 |
| 103 | " | Compound (7) | 95 | 0.75 |
| 111 | Magenta Coupler B | — | 100 | 2.15 |
| 112 | " | Compound (2) | 96 | 0.71 |
| 113 | " | Compound (7) | 97 | 0.59 |
| 121 | Yellow Coupler C | — | 100 | 1.95 |
| 122 | " | Compound (2) | 94 | 0.88 |
| 123 | " | Compound (7) | 98 | 0.90 |

From the results of Table 1, it can be understood that Compound (2) and Compound (7) have a marked effect of softening the gradation without substantial desensitization even though they are used in combination with either cyan, magenta, or yellow couplers.

These samples were subjected to edge exposure using soft X-rays, to the above development processing, and to scanning using a microdensitometer through a red, green or blue filter which is the complementary color of the developed color. As a result, it was found that the samples containing Compound (2) and Compound (7) showed a marked edge effect as compared with those samples not containing the compounds.

EXAMPLE 2

Preparation of Samples 104, 114 and 124

Samples 104, 114 and 124 were produced in the same manner as in Samples 102, 112 and 122, respectively, except that 2-t-octyl-5-(1-phenyltetrazol-5-ylthio)hydroquinone was used in place of Compound (2).

Preparation of Samples 101 to 103, 111 to 113 and 121 to 123

The same as in Example 1.

These samples were allowed to stand in a refrigerator at 10° C for 3 days (Condition A) and separately allowed to stand in a room, in which the temperature and humidity were respectively adjusted to 40° C and 80% RH, for 3 days (Condition B). The samples allowed to stand under different conditions, i.e., Conditions A and B, were subjected to the same exposure, development, and density measurement as in Example 1.

The change in sensitivity between the sample allowed to stand under Condition A and the same sample allowed to stand under Condition B were measured and the results obtained are shown in Table 2. The change in sensitivity is indicated as Δlog (fog + 0.2), i.e., the difference between the former and the latter in log E which corresponds to the optical density at fog + 0.2 in the characteristic curve of the sample.

TABLE 2

| Sample | Addition Layer | Coupler Used in Combination | Compound Added | $\Delta S_{fog+0.2}^{(log\ E)}$ |
|---|---|---|---|---|
| 101 | red-sensitive | cyan coupler | — | −0.05 |
| 102 | " | " | (2) | −0.07 |
| 103 | " | " | (7) | −0.04 |
| 104 | " | " | hydroquinone derivative | −0.23 |
| 111 | green-sensitive | magenta coupler | — | −0.02 |
| 112 | " | " | (2) | +0.01 |
| 113 | " | " | (7) | −0.05 |
| 114 | " | " | hydroquinone derivative | −0.20 |
| 121 | blue-sensitive | yellow coupler | — | −0.00 |
| 122 | " | " | (2) | −0.02 |
| 123 | " | " | (7) | −0.04 |
| 124 | " | " | hydroquinone derivative | −0.17 |

As is apparent from the above results, those samples to which Compounds (2) and (7) were added, have good stability with time as a raw film (i.e., a slight reduction in sensitivity) as compared to those samples to which a DIR hydroquinone (2-t-octyl-5-(1-phenyltetrazol-5-ylthio)hydroquinone) was added.

EXAMPLE 3

Preparation of Coating Solution 10

To 1 kg of a conventional silver iodobromide emulsion (amount of silver: 0.6 mol; iodide content: 6 mol%) was added 280 g of an emulsion which had been prepared by dissolving 100 g of Coupler B in 100 ml of tricresyl phosphate and 200 ml of ethyl acetate, and emulsifying the resulting solution in 1 kg of a 10% aqueous solution of gelatin using 4 g of sodium nonylbenzene sulfonate, which was then stirred.

Preparation of Coating Solution 20

Coating Solution 20 was prepared in the same manner as in preparing Coating Solution 10 except that Compound (2) was further added to the tricresyl phosphate/ethyl acetate mixture of the above emulsion in an amount of 4 mol% based upon Coupler B.

Preparation of Coating Solution 30

Coating Solution 30 was prepared in the same manner as in preparing Coating Solution 20 except that methyl 2-{2-[2',5'-dihydroxy-6'-(1'-phenyltetrazol-5''-ylthio)-3'-n-pentadecylthio]phenylthio}benzoate was used in place of Compound (2).

The above coating solutions were stirred at 40° C for 10 hours and then coated on a transparent cellulose triacetate film support in a silver coating amount of 1.5 g/m². Coating Solutions 11, 21 and 31, which had the same composition as Coating Solutions 10, 20 and 30, respectively, and were, just after the production thereof, i.e., not subjected to the 10 hours of stirring, coated on the same coating support at the same time. The thus-obtained samples were subjected to stepwise exposure using white light and sensitometry according to Example 1.

The results obtained are shown in Table 3.

TABLE 3

| Sample | Coating Solution | Compound | Relative Sensitivity $S_{fog+0.2}$ | γ |
|---|---|---|---|---|
| 210 | 10 | — | 100 | 1.87 |
| 211 | 11 | — | 100 | 1.88 |
| 220 | 20 | (2) | 90 | 0.86 |
| 221 | 21 | (2) | 91 | 0.83 |
| 230 | 30 | hydroquinone derivative | 75 | 1.25 |
| 231 | 31 | " | 98 | 0.96 |

As can be understood from the above results, those coating solutions to which the above hydroquinone derivatives were added were desensitized and hard-toning occurred with time, whereas in the coating solutions to which Compound (2) of the present invention was added no change in photographic properties with time after being dissolved occurred.

EXAMPLE 4

Preparation of Sample 300

1 kg of a conventional silver iodobromide emulsion (amount of silver: 0.4 mol; iodide content: 5 mol%) was coated on a transparent cellulose triacetate film support in a silver coating amount of 1.5 g/m².

Preparation of Sample 301

An emulsion was produced by dissolving 100 g of Compound (2) in 100 ml of tricresyl phosphate and 200 ml of ethyl acetate, and then emulsifying the resulting solution in 1 kg of a 10% aqueous solution of gelatin using 4 g of sodium nonylbenzene sulfonate. 60 g of this emulsion was added to the coating solution of Sample 300 and stirred, which was then coated in the same manner as in Sample 300.

The thus-obtained Samples 300 and 301 were subjected to stepwise exposure using white light, developed using D-76 having the following formulation:

p-Methylaminophenol Sulfate: 2 g
Hydroquinone: 5 g
Sodium Sulfite (anhydrous): 100 g
Borax: 2 g
Water: up to 1 l fixed with an ammonium thiosulfate solution, washed with water, and dried. The degree of silver blackening was then measured.

Sample 310 exhibited soft toning without any reduction in sensitivity, as compared with Sample 300.

On the other hand, Samples 300 and 310 were subjected to edge exposure using soft X-rays, and to the above black-and-white development, and were scanned using a microdensitometer. The results obtained showed that Sample 310 had a marked edge effect as compared with Sample 300.

Thus, it can be understood that Compound (2) exhibits a DIR effect even in black-and-white development.

EXAMPLE 5

On a cellulose triacetate film support were coated in succession the first through eleventh layers having the compositions shown below to thus produce a multilayer color light-sensitive material. The additives marked with an asterisk (*) are the same as in Example 1.

First Layer: Antihalation Layer (AHL)

A gelatin layer containing black colloidal silver

Second Layer: Intermediate Layer (ML)

A gelatin layer containing an emulsion of 2,5-ditert-octylhydroquinone

Third Layer: First Red-Sensitive Emulsion Layer (RL$_1$)

Silver Iodobromide Emulsion (iodide: 5 mol%)
  Silver Coating Amount: 1.79 g/m$^2$
Sensitizing Dye I*
  $6 \times 10^{-5}$ mol per mol of silver
Sensitizing Dye II*
  $1.5 \times 10^{-5}$ mol per mol of silver
Coupler A*
  0.04 mol per mol of silver
Coupler C-1
  0.0015 mol per mol of silver
Coupler C-2
  0.0015 mol per mol of silver
Compound (2)
  0.002 mol per mol of silver Fourth Layer: Second Red-Sensitive Emulsion Layer (RL$_2$)

Silver Iodobromide Emulsion (iodide: 4 mol%)
  Silver Coating Amount: 1.4 g/m$^2$
Sensitizing Dye I*
  $3 \times 10^{-5}$ mol per mol of silver
Sensitizing Dye II*
  $1.2 \times 10^{-5}$ mol per mol of silver
Coupler A*
  0.005 mol per mol of silver
Coupler C-1
  0.0008 mol per mol of silver
Coupler C-2
  0.0008 mol per mol of silver
Coupler C-3
  0.015 mol per mol of silver
Compound (2)
  0.0008 mol per mol of silver Fifth Layer: Intermediate Layer (ML)

Same as the Second Layer

Sixth Layer: First Green-Sensitive Emulsion Layer (GL$_1$)

Silver Iodobromide Emulsion (iodide: 4 mol%)
  Silver Coating Amount: 1.5 g/m$^2$
Sensitizing Dye III*
  $3 \times 10^{-5}$ mol per mol of silver
Sensitizing Dye IV*
  $1 \times 10^{-5}$ mol per mol of silver
Coupler B*
  0.05 mol per mol of silver
Coupler M-1
  0.008 mol per mol of silver
Compound (2)
  0.0015 mol per mol of silver Seventh Layer: Second Green-Sensitive Emulsion Layer (GL$_2$)

Silver Iodobromide Emulsion (iodide: 5 mol%)
  Silver Coating Amount: 1.6 g/m$^2$
Sensitizing Dye III*
  $2.5 \times 10^{-5}$ mol per mol of silver
Sensitizing Dye IV*
  $0.8 \times 10^{-5}$ mol per mol of silver
Coupler B*
  0.02 mol per mol of silver
Coupler M-1
  0.003 mol per mol of silver
Compound (2)
  0.0008 mol per mol of silver Eighth Layer: Yellow Filter Layer (YEL)

A gelatin layer prepared by coating a coating solution containing yellow colloidal silver and a 2,5-di-tertoctylhydroquinone emulsion in a gelatin aqueous solution Ninth Layer: First Blue-Sensitive Emulsion Layer (BL$_1$)

Silver Iodobromide Emulsion (iodide: 6 mol%)
  Silver Coating Amount: 1.5 g/m$^2$
Coupler Y-1
  0.25 mol per mol of silver
Compound (2)
  0.001 mol per mol of silver Tenth Layer: Second Blue-Sensitive Emulsion Layer (BL$_2$)

Silver Iodobromide Emulsion (iodide: 6 mol%)
  Silver Coating Amount: 1.1 g/m$^2$
Coupler Y-1
  0.06 mol per mol of silver Eleventh Layer: Protective Layer (PL)

Prepared by coating a gelatin layer which contained an emulsion of silver iodobromide super fine particles (amount of silver: 0.06 mol per kg; iodide content: 1.4 mol%; average particle size: 0.03 μ), and polymethylmethacrylate particles (diameter: about 1.5 μ).

Compounds shown with "*" are described in Examples.

To each layer were added a suitable amount of a gelatin hardener, a surface active agent, and a thickening agent in addition to the above components.

The thus-prepared sample was designated as Sample 400.

SAMPLE 410

Sample 410 was prepared in the same manner as in Sample 400 except that Compound (2) was not used.

Sample 420

Only the gradation was reduced by reducing the silver coating amounts of the red-sensitive layer, the green-sensitive layer, and the blue-sensitive layer of Sample 410 by about 25%, and the gradation of each layer was adjusted to Sample 400.

Sample 430

Adjusted to the gradation of each layer of Sample 400 by converting each emulsion of the red-sensitive layer, the green-sensitive layer, and the blue-sensitive layer of Sample 410 into an emulsion which was produced by controlling the silver halide precipitation conditions and the amount of the additives to be incorporated into the emulsion prior to coating, and which had equal sensitivity and had a soft tone.

COUPLERS USED IN PREPARING THE SAMPLES

Coupler C-1: 1-Hydroxy-4-[2-(2-hexyldecyloxycarbonyl)phenylazo]-2-[N-(1-naphthyl)]naphthamide Coupler C-2: 1-Hydroxy-4-[4-(ethoxycarbonyl)phenylazo]-2-(N-dodecyl)naphthamide Coupler C-3: 1-Hydroxy-4-iodo-2-(N-dodecyl)naphthamide Coupler M-1: 1-(2,4,6-Trichlorophenyl)-3-hexadecanamido-4-(4-hydroxyphenyl)azo-5-pyrazolone Coupler Y-1: α-(2,4-Dioxo-5,5-dimethyloxazolidinyl)-α-pivaloyl-2-chloro-5-[α-(2,4-di-tert-amylphenoxy)butanamido]-acetanilide The thus-prepared samples were subjected to stepwise exposure using white light, blue light, green light, and red light sources, and sensitometry in the same manner as in Example 1.

Each emulsion layer of Samples 400, 420 and 430 had almost equal sensitivity and gradation, and although Sample 410 had hard tone as compared with other samples, it had equal sensitivity. The particle form of Sample 400 containing Compound (2) was quite fine as compared with all other samples.

These samples were processed into 35 mm size films, and photographed, and the thus-obtained negative films were enlarged and printed. With regard to the obtained color images, Sample 400 had the finest graininess, and was the sharpest, and furthermore, the color was sharp and particularly the reproduction of green was sharp.

These results show that Compound (2) has quite excellent graininess properties, sharpness, and improvement in color reproduction.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a support having thereon at least one light-sensitive silver halide emulsion layer, with a layer of the photographic material containing a photographic developing agent represented by the formula (I):

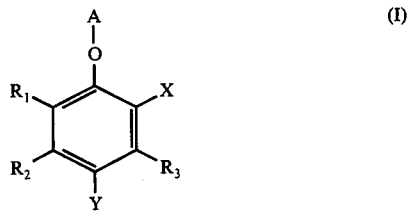

(I)

wherein one of X and Y is a group which inhibits development on release immediately after a developing agent is oxidized at development and is connected to the benzene ring in the agent represented by formula (I) by a sulfur, selenium or nitrogen atom, and the other of X and Y is an —NH—SO$_2$—Z group wherein Z is an alkyl group, an aryl group, or a heterocyclic group; A is a hydrogen atom or a group hydrolyzable under alkaline conditions; R$_1$, R$_2$ and R$_3$, which can be the same or different, each is a hydrogen atom, an alkyl group, an aryl group, a heterocyclic group, an alkoxy group, an aryloxy group, an —S—Z' group wherein Z' is an alkyl group, an aryl group or a heterocyclic group, an —NH—SO$_2$—Z'' group wherein Z'' is an alkyl group, an aryl group or a heterocyclic group, an acylamido group, an amino group, a halogen atom, a hydroxy group, or an acyloxy group; and R$_1$ and R$_2$ further may combine to form a ring.

2. A silver halide photographic light-sensitive material as claimed in claim 1, wherein said photographic developing agent represented by the formula (I) has the formula (II):

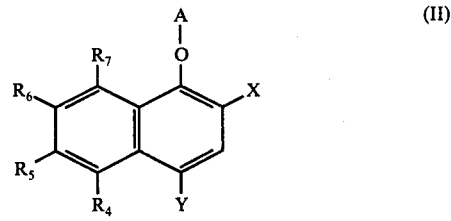

(II)

wherein R$_4$, R$_5$, R$_6$ and R$_7$, which may be the same or different, each represents a hydrogen atom, a halogen atom, a straight or branched alkyl group containing 1 to 30 carbon atoms which may be substituted with one or more of a halogen atom, an alkoxy group, a hydroxy group, a carboxy group, a sulfo group, a heterocyclic group or an aryl group, a straight or branched alkoxy group containing 1 to 30 carbon atoms which may be substituted with one or more of the substituents as described above for the alkyl group, a phenyl group having from 6 to 36 carbon atoms which may be substituted with one or more of a halogen atom, an alkyl group, or an alkoxy group, a phenyloxy group, which may be substituted with one or more of the substituents as defined above for the phenyl group, a 5- or 6-membered heterocyclic group containing one or more of a nitrogen atom, an oxygen atom, or a sulfur atom as a hetero atom, which may be condensed with a benzene or naphthylene nucleus, an acylamino group, a sulfonamido group, a carbamoyl group, a sulfamyl group, an acyl group, an alkoxycarbonyl group or an alkylthio group, and wherein X, Y and A are as defined in claim 1.

3. A silver halide photographic light-sensitive material as claimed in claim 1, wherein said photographic developing agent represented by the formula (I) has the formula (III):

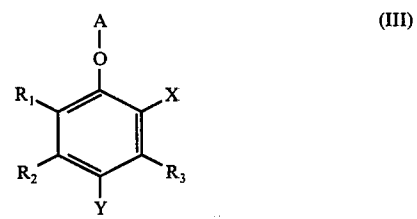

(III)

wherein one of X and Y is a group capable of inhibiting development on release immediately after a developing agent is oxidized at development, and the other of X and Y is an —NHSO$_2$—Z group, wherein Z contains 1 to 30 carbon atoms and is an alkyl group, an aryl group, or a 5- or 6-membered heterocyclic group; A is a hydrogen atom or a group hydrolyzable under alkaline conditions; R$_1$, R$_2$ and R$_3$, which may be the same or different, is a hydrogen atom, a halogen atom, an alkyl group containing 1 to 30 carbon atoms, an alkoxy group containing 1 to 30 carbon atoms, an aryl group, an aryloxy group, an amino group, an —SZ' group, or an —NHSO$_2$Z'' group, wherein Z' and Z'', which may be the same or different, each is as described above for Z, and R$_1$ and R$_2$ further may combine together to form a saturated or unsaturated ring.

4. A silver halide photographic light-sensitive material as claimed in claim 1, wherein said group capable of inhibiting development on release for X and Y is a group containing a sulfur atom or a nitrogen atom therein through which said group is bonded to the developing agent mother nucleus.

5. A silver halide photographic light-sensitive material as claimed in claim 4, wherein said group capable of inhibiting the development on release for X and Y is an arylthio group, a heterocyclic thio group, a group derived from a thioglycolic acid based compound, a group derived from a cystein based compound or a group derived from a glutathion based group.

6. A silver halide photographic light-sensitive material as claimed in claim 1, wherein said group capable of inhibiting development on release for X and Y is a triazolyl group.

7. A silver halide photographic light-sensitive material as claimed in claim 1, wherein Z is a straight or branched alkyl group containing 1 to 30 carbon atoms which may be substituted with one or more of a halogen atom, an alkenyl group, an alkoxy group, a hydroxy group, an aryloxy group, a carboxy group, an alkoxycarbonyl group, an aryloxycarbonyl group, a sulfo group, a heterocyclic group, or an aryl group, an aryl group which may be substituted with one or more of a halogen atom, an alkyl group, an alkoxy group, a nitro group, a cyano group, an acyl group, a carboxy group, an alkoxycarbonyl group, an acylamino group, a carbamoyl group, a sulfamoyl group, or a sulfo group, a 5- or 6-membered heterocyclic group containing one or more of a nitrogen atom, an oxygen atom, or a sulfur atom as a hetero atom, which may be condensed with a benzene or naphthylene nucleus; wherein $R_1$, $R_2$ and $R_3$, which can the same or different, each is a hydrogen atom, a halogen atom, a straight or branched alkyl group having 1 to 30 carbon atoms which may be substituted with one or more of a halogen atom, an alkoxy group, a hydroxy group, a carboxy group, a sulfo group, a heterocyclic group or an aryl group, a straight or branched alkoxy group containing 1 to 30 carbon atoms in which the alkyl moiety thereof may be substituted with one or more of a halogen atom, an alkoxy group, a hydroxy group, a carboxy group, a sulfo group, a heterocyclic group or an aryl group, an acylamino group, an aryl group containing 6 to 36 carbon atoms which may be substituted with one or more of a halogen atom, an alkyl group, or an alkoxy group. an aryloxy group containing 6 to 36 carbon atoms in which the aryl moiety thereof may be substituted with one or more of a halogen atom, an alkyl group, or an alkoxy group, a 5- or 6-membered heterocyclic group containing one or more of a nitrogen atom, an oxygen atom, or a sulfur atom as a hetero atom, which may be condensed with a benzene nucleus or naphthylene nucleus, an amino group, which may be substituted with one or more of an alkyl group, an aryl group or a heterocyclic group containing up to 30 carbon atoms as substituents, an —SZ' group or an —NHSO$_2$Z'' group wherein Z' and Z'', which may be the same or different, each is as defined for Z and wherein the ring formed when $R_1$ and $R_2$ combine is a saturated or unsaturated ring which may be substituted with those groups as defined above for $R_1$, $R_2$ and $R_3$ as substituents.

8. A multi-layer color light-sensitive material comprising a support having thereon a blue-sensitive emulsion layer comprising at least one blue-sensitive silver halide emulsion layer containing a yellow image-forming coupler, a green-sensitive emulsion layer comprising at least one green-sensitive silver halide emulsion layer containing a magenta image-forming coupler, and a red-sensitive emulsion layer comprising at least one red-sensitive silver halide emulsion layer containing a cyan image-forming coupler, said light-sensitive material further containing a photographic developing agent in at least one of said emulsion layers or an intermediate layer additionally present, wherein said photographic developing agent is represented by the formula (I):

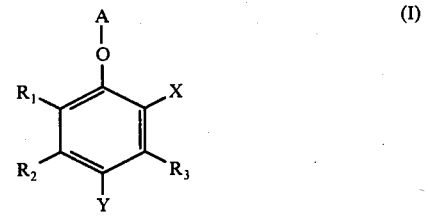

wherein one of X and Y is a group which inhibits development on release immediately after a developing agent is oxidized at development and is connected to the benzene ring in the agent represented by formula (I) by a sulfur, selenium or nitrogen atom, and the other of X and Y is an —NH—SO$_2$—Z group wherein Z is an alkyl group, an aryl group, or a heterocyclic group; A is a hydrogen atom or a group hydrolyzable under alkaline conditions; $R_1$, $R_2$ and $R_3$, which can be the same or different, each is a hydrogen atom, an alkyl group, an aryl group, a heterocyclic group, an alkoxy group, an aryloxy group, an —S—Z' group wherein Z' is an alkyl group, an aryl group or a heterocyclic group, an —NH—SO$_2$—Z'' group wherein Z'' is an alkyl group, an aryl group or a heterocyclic group, an acylamido group, an amino group, a halogen atom, a hydroxy group, or an acyloxy group; and $R_1$ and $R_2$ further may combine to form a ring.

9. A multi-layer color light-sensitive material as claimed in claim 8, wherein said photographic developing agent represented by the formula (I) has the formula (II):

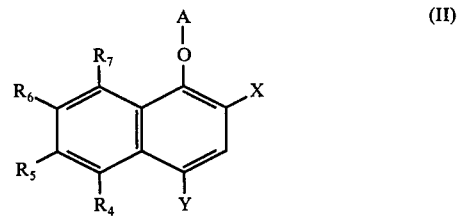

wherein $R_4$, $R_5$, $R_6$ and $R_7$, which may be the same or different, each represents a hydrogen atom, a halogen atom, a straight or branched alkyl group containing 1 to 30 carbon atoms which may be substituted with one or more of a halogen atom, an alkoxy group, a hydroxy group, a carboxy group, a sulfo group, a heterocyclic group or an aryl group, a straight or branched alkoxy group containing 1 to 30 carbon atoms which may be substituted with one or more of the substituents as described above for the alkyl group, a phenyl group having from 6 to 36 carbon atoms which may be substituted with one or more of a halogen atom, an alkyl group, or an alkoxy group, a phenyloxy group, which may be substituted with one or more of the substituents as defined above for the phenyl group, a 5- or 6-membered heterocyclic group containing one or more of a nitrogen atom, an oxygen atom, or a sulfur atom as a hetero atom, which may be condensed with a benzene or naphthylene nucleus, an acylamino group, a sulfonamido group, a carbamoyl group, a sulfamyl group, an acyl group, an alkoxycarbonyl group or an alkylthio group, and wherein X, Y and A are as defined in claim 8.

10. A multi-layer color light-sensitive material as claimed in claim 8, wherein said photographic developing agent represented by the formula (I) has the formula (III):

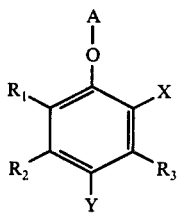

wherein one of X and Y is a group capable of inhibiting development on release immediately after the developing agent is oxidized at development, and the other of X and Y is an —NHSO$_2$—Z group, wherein Z contains 1 to 30 carbon atoms and is an alkyl group, an aryl group, or a 5- or 6-membered heterocyclic group; A is a hydrogen atom or a group hydrolyzable under alkaline conditions; $R_1$, $R_2$ and $R_3$, which may be the same or different, is a hydrogen atom, a halogen atom, an alkyl group containing 1 to 30 carbon atoms, an alkoxy group containing 1 to 30 carbon atoms, an aryl group, an aryloxy group, an amino group, an —SZ' group, or an —NHSO$_2$Z" group, wherein Z' and Z", which may be the same or different, each is as described above for Z, and $R_1$ and $R_2$ further may combine together to form a saturated or unsaturated ring.

11. A method of forming an image comprising developing an imagewise exposed silver halide photographic light-sensitive material having thereon at least one light-sensitive silver halide emulsion layer in the presence of a photographic developing agent represented by the formula (I):

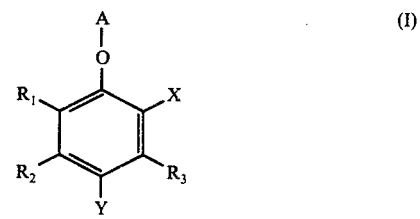

wherein one of X and Y is a group which inhibits development on release immediately after a developing agent is oxidized at development and is connected to the benzene ring in the agent represented by formula (I) by a sulfur, selenium or nitrogen atom, and the other of X and Y is an —NH—SO$_2$—Z group wherein Z is an alkyl group, an aryl group, or a heterocyclic group; A is a hydrogen atom or a group hydrolyzable under alkaline conditions; $R_1$, $R_2$ and $R_3$, which can be the same or different, each is a hydrogen atom, an alkyl group, an aryl group, a heterocyclic group, an alkoxy group, an aryloxy group, an —S—Z' group wherein Z' is an alkyl group, an aryl group or a heterocyclic group, an —NH—SO$_2$—Z" group wherein Z" is an alkyl group, an aryl group or a heterocyclic group, an acylamido group, an amino group, a halogen atom, a hydroxy group, or an acyloxy group; and $R_1$ and $R_2$ further may combine to form a ring.

12. The method of forming an image of claim 11, wherein the silver halide photographic light-sensitive material comprises a support having thereon a blue-sensitive silver halide emulsion layer containing a yellow image-forming coupler, a green-sensitive silver halide emulsion layer containing a magenta image-forming coupler and a red-sensitive silver halide emulsion layer containing a cyan image-forming coupler.

* * * * *